(12) United States Patent
Hagen et al.

(10) Patent No.: US 12,702,748 B2
(45) **Date of Patent: *Aug. 11, 2026**

(54) ENEMA DEVICE AND A METHOD OF REFILLING SAID DEVICE WITH AN ENEMA

(71) Applicant: QUFORA A/S, Allerød (DK)

(72) Inventors: Thit Rose Hagen, Roskilde (DK); Ana Latorre Duque, Alcorisa (ES)

(73) Assignee: QUFORA A/S, Allerød (DK)

( * ) Notice: Subject to any disclaimer, the term of this patent is extended or adjusted under 35 U.S.C. 154(b) by 1121 days.

This patent is subject to a terminal disclaimer.

(21) Appl. No.: 17/724,549

(22) Filed: Apr. 20, 2022

(65) Prior Publication Data

US 2022/0249765 A1 Aug. 11, 2022

Related U.S. Application Data

(63) Continuation of application No. 16/626,117, filed as application No. PCT/DK2018/050169 on Jun. 28, 2018, now Pat. No. 11,331,422.

(30) Foreign Application Priority Data

Jun. 30, 2017 (DK) .................................. 201770531

(51) Int. Cl.
*A61M 3/02* (2006.01)

(52) U.S. Cl.
CPC ......... *A61M 3/0262* (2013.01); *A61M 3/0245* (2013.01); *A61M 2205/071* (2013.01)

(58) Field of Classification Search
CPC .......... A61M 3/0262; A61M 2205/071; A61M 3/02; A61K 9/065
See application file for complete search history.

(56) References Cited

U.S. PATENT DOCUMENTS 3,071,136 A * 1/1963 Nordstrom .......... A61M 3/0262 604/212
3,507,280 A * 4/1970 Pollock ............... A61M 3/0262 604/911
4,136,696 A * 1/1979 Nehring, John R. ........................ A61M 3/0262 604/142
4,168,032 A * 9/1979 Sneider ................ B05B 11/047 222/215

(Continued)

FOREIGN PATENT DOCUMENTS

EP 4616878 A1 * 9/2025 ............. A61K 47/36

*Primary Examiner* — Lauren P Farrar
(74) *Attorney, Agent, or Firm* — Fox Rothschild LLP

(57) ABSTRACT

The present invention relates to an enema device comprising a delivery container and an applicator nozzle, and wherein said delivery container comprises two cavities, an outer cavity defined by a squeezable external body, and an inner cavity defined by an inner flexible bladder, and wherein one of said cavities is communicating with an outlet for dispersing the enema though the applicator nozzle and the other cavity is communicating with the surroundings via an air inlet. Thereby is provided a simple, inexpensive and essentially maintenance free enema device which can be used for self-administrating of an enema. The device will not only effectively prevent air from being mixed with the enema, but also ensure that the user easily can expel the enema, as the device will be perceived as full of enema at all times.

31 Claims, 4 Drawing Sheets

(56) References Cited

U.S. PATENT DOCUMENTS

Figure 2:
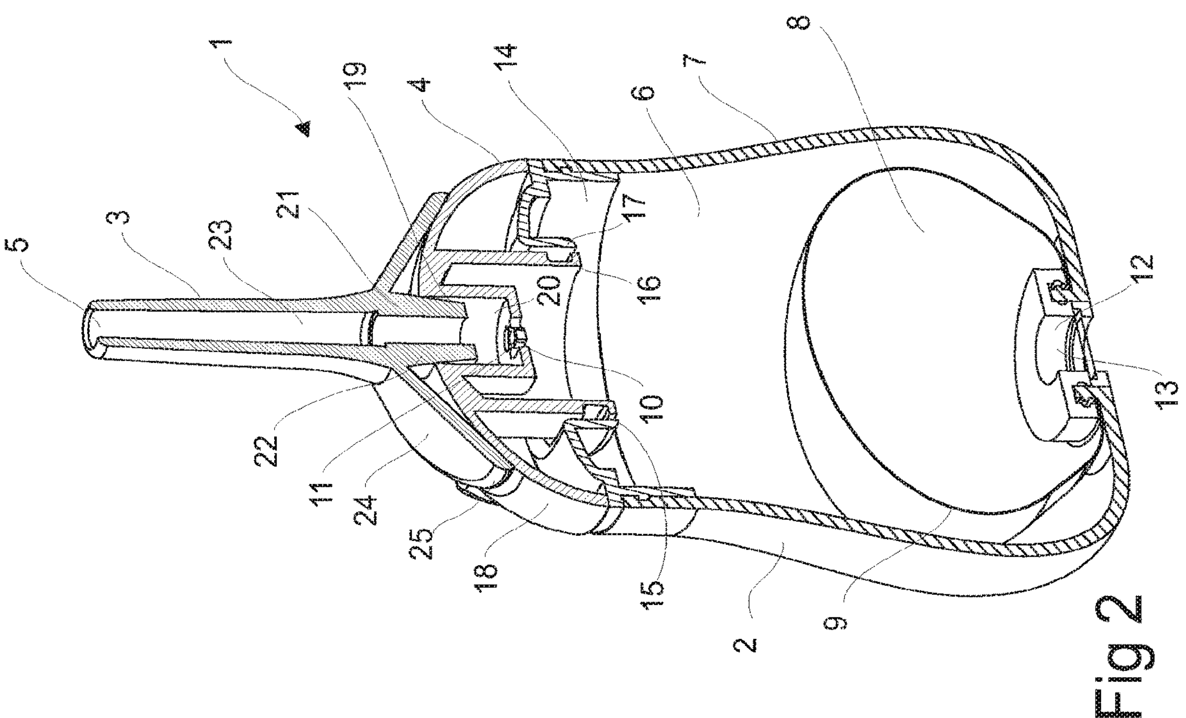

| | | | | |
|---|---|---|---|---|
| 2012/0310174 | A1* | 12/2012 | Yoo | A61M 3/0262<br>604/212 |
| 2019/0046744 | A1* | 2/2019 | French | A61M 15/08 |

* cited by examiner 5
3
1
24
19
4
14
6
7
10
15
9
2
8
12

5
3
1'
23
24
19
4
14
15
10
8'
7'
12
9'
6'

ENEMA DEVICE AND A METHOD OF REFILLING SAID DEVICE WITH AN ENEMA

This application is a Continuation of application Ser. No. 16/626,117 filed on Dec. 23, 2019. Application Ser. No. 16/626,117 is a National Phase of International Patent Application No. PCT/DK/2018/050169, filed Jun. 28, 2018, and claims priority from Application PA 201770531 filed on Jun. 30, 2017 in Denmark. The entire contents of these applications are incorporated herein by reference in their entirety.

The present invention relates to an enema device comprising a flexible delivery container and an applicator nozzle.

Administrating an enema is a common medical procedure whereby fluid is injected into the rectum and lower intestine of a patient in order to induce bowel movement. The need for such a procedure typically arises in patients suffering from certain physical ailments in which voluntary bowel control is impaired or when the bowel needs to be cleaned before e.g. a coloscopy or a surgical operation.

Medical equipment currently exists in the art for administering an enema to patients in need of this procedure. At least one type of equipment consists of an enema squeeze bottle filled with the fluid intended to induce bowel movement, which is capped by a short applicator nozzle to be inserted into the patient's rectum. The applicator nozzle of this type of conventional enema application device often causes discomfort and irritation when being inserted.

Furthermore, the force required to squeeze the liquid from an enema dispenser affects the ease with which a user may administer the liquid. The self-administration of a conventional enema may be especially difficult for patients have poor dexterity, e.g. due to the squeeze force required to deliver a complete dose of the enema liquid.

Although it would be advantageous to decrease the amount of squeeze force required to administer an enema, such a modification may adversely affect other desirable features of the device. In particular, it is desirable to prevent any reflux of liquid back into the delivery container after the enema liquid has been delivered, and it is desirable to prevent leakage of the enema liquid from the dispenser prior to use. A simple reduction in the resistance to flow of the liquid through the device may compromise these features.

Moreover, enemas are often administered to a patient at home when the need for medical assistance does not necessitate a doctor or another health care assistant.

However, it is often difficult for the patient to administer the enema to him or herself since the applicator nozzle not only must be inserted into a sensitive area, but the administration position is also inconvenient for the user making it is difficult for the patient to administer the liquid while steadily holding the enema in the required area. Often the patient is assisted by another individual; however, assistance may not always be available, if, for instance, the patient lives alone. Thus, there is also a need for an enema device that can be effectively self-administered.

Such an enema device is e.g. known from WO2010122537, disclosing a device which can be used for administrating an enema. Said enema device ensures that uncontrolled flow of liquid into or out of the device is prevented by using two one-way valves, one for delivering the liquid and one for refilling the device. As the device is compact the device can easily be held in a single hand making the device suitable for home-administration of an enema.

The enema is administered by squeezing the delivery container, and after releasing the compression force, the container may either be re-inflated by drawing surrounding air into the container via a first one-way valve, or the container may be re-loaded with enema by drawing enema into the container.

The latter will ensure that the device can be used for several administrations as needed by the user, however studies and user feed-back have shown that most users does not have the strength to provide a constant pressure on the delivery container. Accordingly, the user will first administer a small amount of enema, then release the pressure on said container and after a short period administering a further small amount of enema. However, when pressure is released on the delivery container, air will unintentionally be drawn into the container and mixed with the enema. Air will then be delivered to the colon when the next dosage of enema is administered. This will cause uncomfortable distending of the colon causing pain and cramps. Thus, in order to avoid intake of air, the user will have apply a constant pressure to the delivery container during the administrating procedure, which may be difficult for users/patients having weak fingers, e.g. due to arthritis or the like.

Furthermore, as air is drawn into the container, expelling of the enema becomes increasingly more difficult. Due to density differences between air and the enema, the device has to be oriented correctly, in order to prevent or reduce administration of air. However, ensuring such an orientation is almost impossible as the enema often is administered on the toilet or in the bed, where the user's/patient's position prevents such an orientation.

Since administration of air will cause discomfort several reloadings of the container with enema are often required in order to deliver an effective dosage of enema and at the same time prevent delivery of air. However, reloading of the container requires easy access to the enema. If the enema for instance is tap water, a user sitting on the toilet, may use the sink as a enema reservoir, however, often the toilet and the sink are to far apart for this to be manageable. Thus, the user has to have a reservoir of enema nearby in order to provide easy reloading, making the reloading both difficult and troublesome.

Thus, there is a demand for a new enema device, which is simple and easy to use and which solves the limitations and disadvantages of the prior art.

It is therefore a first aspect of the present invention to provide a handheld enema device that safely and effectively can administer an enema to a patient without causing discomfort.

It is a second aspect of the present invention to provide an enema device where the liquid is easier to administer, and where air effectively is prevented from being mixed with the enema.

It is a third aspect of the present invention to provide an enema device in which an effective dosage of enema can be administered without required reloading of the delivery container.

It is a forth aspect of the present invention to provide an enema device that prevents reflux of liquid into the container after use and/or prevents leakage of the fluid prior to use.

In a fifth aspect according to the present invention is provided an enema device that is inexpensive to manufacture and is simple and reliable to use.

In a sixth aspect according to the present invention is provided an enema device that is relatively small and easy to operate, especially by one hand.

In a seventh aspect according to the present invention is provided an enema device arranged to delivery an enema to a patient sitting on the toilet, without requiring reloading with enema.

The novel and unique whereby these and further aspects are achieved is the fact that the enema device comprises a delivery container and an applicator nozzle, and wherein said delivery container comprises two cavities, an outer cavity defined by an squeezable external body, and an inner cavity defined by an inner flexible bladder, and wherein one of said cavities is communicating with an outlet for dispersing the enema though the applicator nozzle and the other cavity is communicating with the surroundings via an air inlet.

Thereby is provided a simple, inexpensive and essentially maintenance free enema device which can be used for administrating enema. The device according to the invention will not only effectively prevent air from being mixed with the enema, but also ensure that the user easily can expel the enema, as the container will be perceived as full of enema, at all times.

In order to ensure that the enema is administered with a relatively high patient compliance, the enema device according to the invention comprises an applicator nozzle preferably arranged for alleviating the physical discomfort and pain that the patient may expire during insertion of the applicator nozzle.

In a first embodiment according to the present invention the outer cavity is communicating with the outlet, and the inner cavity is communicating with the surroundings. The enema is accordingly accommodated/placed in the outer cavity (the enema cavity) thus, when the user squeezes the container the enema will be expelled from the outer cavity though the applicator nozzle via the outlet.

When the user during the administration procedure releases the compression force on the container, air will be drawn into the inner flexible bladder via the air inlet. Since the inner and outer cavity cannot communicate with each other, air in the inner cavity is effectively prevented from being mixed with the enema in the outer cavity. Accordingly, air cannot be administered into the patients colon and unnecessary discomfort caused by distending of the colon by air, is effectively prevented.

Drawing air into the inner cavity, i.e. the flexible bladder (air cavity) further has the advantage that the size of said bladder increases, causing a change in the respective sizes of the cavities, i.e. when the size of the flexible inner cavity (containing air) increases as air is drawn into said cavity, the size of the outer cavity (containing enema) is reduced. Thus, the air in the inner cavity will function as a displacement fluid, forcing the enema in the outer cavity towards the outlet. In this way the enema device will always be perceived as "full of enema" by the user until the desired dosage, or the entire enema content, has been expelled from the device.

Thereby the unique construction of the enema device according to the present invention ensures that the user can release the pressure on the container during the administration procedure without having to worry about air being mixed with the enema. Furthermore, as air is drawn into the flexible bladder the size of the enema cavity is reduced whereby enema easily can be expelled from the device by squeezing the delivery container. Thereby is provided an enema device which is highly suitable for self-administration, as the effort required to expel the enema liquid is significantly reduced compared to the known enema devices.

In a second embodiment according to the present invention, the placement of the enema and air is reversed, i.e. the enema is placed in the flexible bladder, becoming the enema cavity, and which accordingly will be communicating with the outlet. Air will be drawn into the outer cavity (air cavity) though the air inlet. Thus, when air is drawn into the outer cavity, the size of the inner cavity containing the enema will be reduced, ensuring that enema always will be placed at the outlet, such that the container will be considered full of enema during use.

The respective cavity accommodating the enema may, as discussed above, be either the inner or the outer cavity, depending on the embodiment. The same applies for the cavity accommodating air as the displacement fluid, which will be the cavity not containing the enema. However, the enema will be accommodated in the cavity communicating with the outlet and air will be accommodated in the cavity communicating with the air inlet. Accordingly, the obtained results and respective changes in sizes of the cavities are the same for the two embodiments. The air cavity will become larger during intake of air, making the enema cavity smaller, whereby the enema is displaced towards the outlet. In this way the enema device according to the invention, will, as long as enema is present in said device, be perceived as full of enema, irrespectively of the actual content of enema.

When the entire content of enema has been expelled from the delivery container, the air cavity will preferably fill out the main, or the entire, inner volume of the squeezable external body. As the air in said cavity neither can be removed from the delivery container nor be compressed, emptying the enema completely can be felt by the user as a change in the hardness of the delivery container, thereby providing a simple indication to the user, that the entire dosage of enema has been administered.

In a preferred embodiment the enema device according to the invention has a size and dimension which ensures that the cavity accommodating the enema, can accommodate at least an effective dosage of enema, preferably slightly more.

Within the context of the present invention the term "an effective dosage of enema" means the amount of enema which is required and/or sufficient for stimulating stool evacuation in the patient. Even though an effective dosage is individual, among others depending on the age of patient (e.g. child vs. adult) administration of enemas is well known in the art, and a person skilled in the art will have no problem of establishing an effective dosage of enema.

In one embodiment, the enema device can accommodate at least about 90 ml of enema, and preferably at least about 130 ml which is slightly more than a conventional enema dosage for most adults. As the required amount of enema is individual, the enema device may in some preferred embodiments accommodate about 150 ml, however the dimensions of said enema device may be adjusted to accommodate a higher or lower amount of enema, within the content of the present invention.

Using an enema device arranged for accommodating an effective dosage of enema, ensures that the user can administer a full and effective dosage of enema, without having to reload the device, and without having to worry about air being mixed with the enema. Accordingly, the patient/user can release the pressure on the delivery container as may times as desired, and the administration of the enema can take as long as the patient need or require without compromising the function of the enema device according to the invention, whereby a high patient compliance is provided.

In a preferred embodiment, a first non-return valve is placed in communication with the outlet. Thus, when the patient/user released the compression force on the delivery container, the first non-return valve will effectively prevent backflow of liquid and faeces from the colon and/or rectum into the enema device. Accordingly, any contamination of the delivery container and it's remaining content, which may occur during and/or after administration of the enema to a patient is precluded.

In a similar manner the air inlet may be placed in communication with a second non-return valve, in order to ensure that air cannot escape the air cavity during the administration process.

Such non-return valves are well known in the art, and may be any valve capable of provide the desired properties to the device according to the invention e.g. swing valves, ball valves, diaphragm valves, butterfly valves, and the like.

As the applicator nozzle is inserted in the rectum during the administrating procedure, it is preferred that the air inlet is placed/located on the enema device at a position distinct/separate from the outlet/applicator nozzle, such that that air can be drawn into the air cavity during use. In a preferred embodiment the air inlet is placed opposite the outlet/applicator nozzle, as this ensures that the air inlet always is free to communicate with the surrounding air, even during administration of the enema. However other suitable positions for the air inlet is also contemplated within the scope of the present invention e.g. in the side of the delivery container.

In order to facilitate refilling and re-use of the enema device according to the invention, it is preferred that the enema device can be restored to an initial position, i.e. a position where the enema device is ready for a new enema administration procedure. It is in this respect preferred, that the enema device is arranged for deflating the air cavity, such that said device can be reused, and that the enema device is arranged for being opened and closed, in order to allow an easy refilling of the enema cavity with enema.

In order to ensure that the enema device according to the invention can be opened and closed, it is preferred that said enema device comprises a closure member which is arranged for being releasable attached to the delivery container, e.g. by means of a first coupling unit. Said first coupling unit may e.g. comprise a first coupling part placed on the closure member and a second coupling part attached to the delivery container. The first coupling unit may be any conventional coupling unit that provides a fluid tight seal between the respective parts, and ensures that the enema device can be opened and closed by either opening or removing the closure member. Such coupling units are known in the art and includes threaded coupling unit, snap-fit coupling units, closable lids, hinged closable lids, etc.

In a simple embodiment the outlet is placed in the closure member, and the closure member is arranged such that when the closure member is opened/removed there is only access to the cavity communicating with the outlet, i.e. the cavity for the enema, whereby an easy manual refilling of enema is possible. Thus, with the closure member is opened/removed there is no access to the cavity communicating with the surroundings via the air inlet.

It is furthermore preferred that the enema device is arranged for releasing the air in the air cavity to the surroundings when the closure member is opened/removed from the delivery container. The air may preferably be released through a release valve that is arranged for being activated when the closure member is removed/opened. Said release valve may e.g. be activate due to a pressure drop in the enema cavity or said release valve may be a pressure relief valve, thus when the pressure in the air cavity exceeds a predetermined limit, the release valve will automatically be activated and deflate the air cavity. Alternatively, there can be a physically connection between the release valve and the closure member thus, when the closure member is removed/opened, said physically connection will activate the release valve. Said release valve is preferably placed near the second non-return valve, i.e. near the air inlet as this will provide a simple construction.

In a preferred embodiment the air inlet and the release valve is combined in a dual function valve. Said dual function valve is arranged as a non-return valve when the closure member closes the delivery container, i.e. when the enema device is ready for the administration procedure, however when the closure member is removed from the delivery container, i.e. when pressure in the enema cavity is reduced, the dual function valve is arranged for allowing air to flow in the opposite direction, deflating the air cavity.

Thus, when air is drawn into the air cavity, the dual function valve function as a non-return valve preventing air drawn into the air cavity from escaping unintentionally during the administration procedure, and when the closure member is removed from the delivery container, the pressure inside the enema cavity drops whereby the dual function valve will allow the air in the air cavity from escaping though the air inlet, i.e. the valve allows air to flow in the opposite direction. Preferred examples of such a dual function valve is one or more of a diaphragm valve, a lip valve; a duck bill valve, an umbrella valve, and/or a dome valve. In a preferred embodiment the dual function valve is a combination valve, e.g. a umbrella/duckbill combination valve.

After the air cavity has been emptied, the user can easily refill the enema cavity with enema, and refit the closure member on the delivery container, whereby the enema device according to the invention is ready for the next enema administration.

The closure member may in one embodiment be made of a rigid material, e.g. polypropylene or polyvinyl chloride, thereby ensuring that the applicator nozzle can be releasable attached to the closure member in communication with the outlet. Said applicator nozzle may be attached to the closure member in any conventional and convenient way, e.g. using a snap-fit, or the like.

In order to ensure a fluid tight seal between the closure member and the deliver container, said closure member may preferably be attached to the delivery container via an intermediate member. Said intermediate member is preferably also made of a rigid material, and may be permanently connected to the delivery container.

The outer cavity is preferably arranged as a hand held pump and is accordingly made of a resilient deformable material with a memory, e.g. silicone. This means that the user can apply pressure on the outer cavity, forcing enema out though the outlet, and when the pressure is released on the outer cavity, the outer cavity will return to the original shape.

The inner flexible bladder defining the inner cavity is preferably made of a material arranged for expanding/unfolding and collapsing in response to the amount of fluid (air or enema) placed in said cavity, prevents any exchange of fluid between the inner and outer cavity, and does not react with the enema and air.

Preferred materials meeting the above definitions are film and/or sheets, e.g. polymer films made of polyethylene, polypropylene, silicone, nitrile, isoprene and/or laminates containing one or more of these. However other suitable materials are also contemplated within the scope of the present invention.

In order to facilitate an ergonomic handling of the device according to the invention the delivery container may have a shape arranged to fit into the users hand, e.g. an elongated spherical shape, a bulb shape or the like. This will not only ensure a pleasant and comforting fit in the hand but will also reduce the necessary force needed to compress the container as well as reducing any awkward postures.

It is furthermore preferred that the enema device according to the invention is small and compact, i.e. that the parts of the enema device is closely packed or joined in order to ensure that the device take up as little spatial space or volume as possible. This will not only ensure that the device can be handheld and easily operated e.g. with a single hand, but also that the enema device easily can be fitted into a hand bag or the like.

The term "enema" covers any liquid, which is capable of promoting bowel movement when introduced into the rectum and colon, such as an enema liquid. Examples of enema liquids include water; hypertonic aqueous salt solutions; solutions or suspensions of cathartic agents, such as bisacodyl or phenolphthalein; and mineral oil. Other liquids capable of promoting bowel movements are well known in the art, and are also contemplated within the scope of the present invention. It is however preferred that the enema has a low viscosity that ensures that the enema easily can be distributed evenly in the colon, e.g. a viscosity corresponding to or being close to the viscosity of water. Gels or liquids having a high viscosity i.e. they cannot flow easily, is accordingly not preferred.

The applicator nozzle may have any shape so long as the nozzle is able to perform the function of administrating the enema to the patient's rectum and/or colon. In a preferred embodiment the applicator nozzle has a mainly fructoconical shape whose outside diameter progressively decreases from it's proximal end to it's distal as said shape automatically will ensure a tight fit with the anal opening.

The applicator nozzle can furthermore be modified in size, shape and possibly other physical properties such as flexibility, rigidity and pliancy to become a plug that accommodates forming a sealing fit with the anal opening. For example, if at least the nozzle is somewhat pliable, it will conform to the shape of the patient's rectum and aid in alleviating the physical discomfort and pain that the patient may expire during insertion of the nozzle.

The nozzle can furthermore be provided with e.g. a pointed blunt tip in order to further reduce said discomfort, a lubricant or an activated hydrophilic coating in order to aid the insertion of the nozzle in the rectum by reducing frictional force.

The applicator nozzle can preferably be disposable in order to reduce contamination of the surroundings e.g. by providing a nozzle, which can be flushed down the toilet after use. This will also make the device more convenient and hygienic in use, however said nozzle may also, if desired, be arranged for being reused after being cleaned and/or sterilised. In any case it is preferred that the applicator nozzle is made of a hypoallergenic material that is non-reactive with the patient's tissue.

The invention also relates to a method of refilling the enema device according to the present invention with an enema. The method comprising the following steps:

a) opening the delivery container, b) deflating the cavity communicating with the air inlet, c) refilling the cavity communicating with the outlet with an enema, and d) closing the delivery container.

It is preferred that the delivery container is opened by opening the closure member, and that air in the air cavity automatically is expelled to the surroundings when the closure member is opened/removed from the delivery container.

The device according to the invention is not only relatively small, having in a preferred embodiment an total length in assembled state of less than 25 cm, preferably less than 15 cm, but also has a simple and user-friendly design, making it extremely easy to operate with a single hand ensuring that the device can be unassistedly used in privacy.

Figure 1:
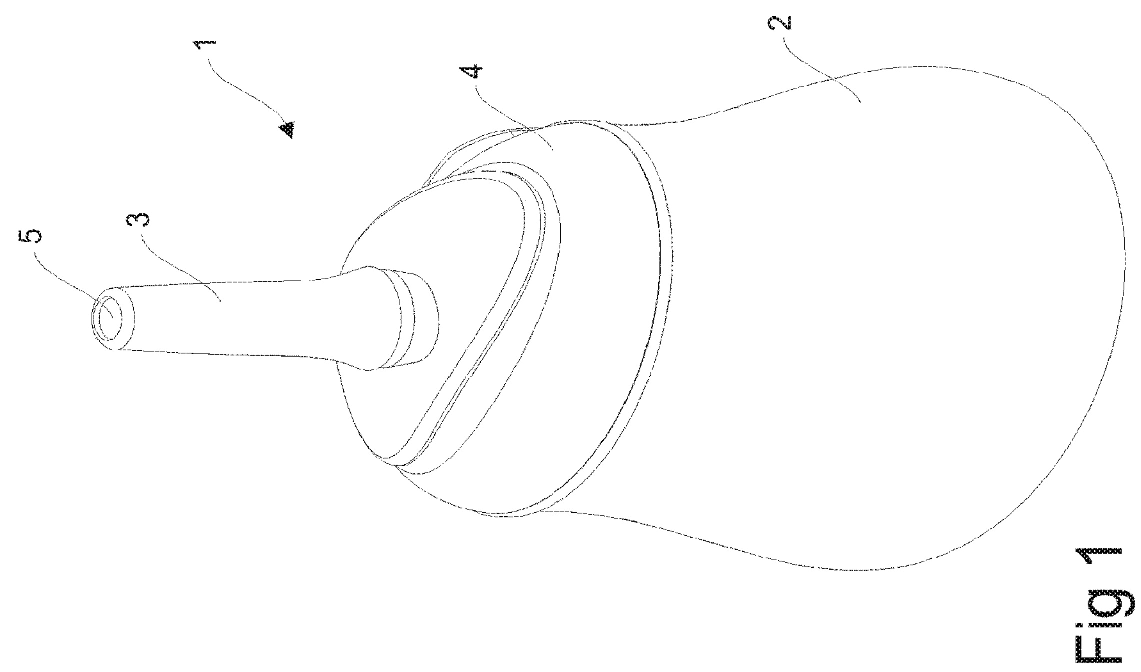

The invention will be explained in greater detail below, describing only exemplary embodiments of the enema device with reference to the drawing, in which FIG. 1 shows a perspective view of a first embodiment of an enema device according to the present invention, FIG. 2, is a sectional view of the first embodiment of an enema device according to the invention, FIG. 3*a*-3*d* schematically illustrates the administration procedure using the first embodiment of the enema device according to the invention, FIG. 4. is a sectional view of a second embodiment of an enema device according to the invention, and FIG. 5*a*-5*d* schematically illustrates the administration procedure using the second embodiment of the enema device according to the invention.

The invention is described below with the assumption that the device according to the present invention is substantially bulb shaped in order to provide a convenient grip for the user. This assumption is not to be construed as limiting, and other shapes e.g. elongated, circular, oval or the like, is also contemplated within the scope of the invention, it is however preferred that the device has a size which facilitates administration by a single hand.

FIG. 1. is a schematic view of a first embodiment of the enema device 1 according to the invention. Said device consist basically of a enema delivery container 2, having a substantially bulb shape, an applicator nozzle 3 and a closure member 4. The applicator nozzle 3 has an exit opening 5 through which the enema can be expelled when pressure is applied to the delivery container 2.

A sectional view of said first embodiment 1 is shown in FIG. 2 wherein the delivery container 2 comprises two cavities, an outer cavity 6 being defined by an squeezable external body 7, and an inner cavity 8 being defined by an inner flexible bladder 9. The outer cavity 6 is in flow communicating with the exit opening 5 via an outlet 10, Thus enema placed in said outer cavity 6 can easily be expelled through the exit opening 5 when pressure/compression force is placed on the delivery container 2 via the squeezable external body 7.

The outlet 10 is a first non-return valve 11 placed in the closure member 4, and said non-return valve 11 will effectively prevent backflow of liquid and faeces from the colon and/or rectum into the enema device 1 when pressure is released on the squeezable external body 7. Accordingly, any contamination of the delivery container 2 and it's remaining content, which may occur during and/or after administration of the enema to a patient, is prevented.

In a similar manner the inner cavity 8 is communicating with the surroundings via an air inlet 12, in the form of a second non-return valve 13, which in the embodiment shown may be a combination valve, such as a umbrella/duckbill combination valve. Said second non-return valve will allow air to be drawn into the inner cavity 8 when pressure is released on the squeezable external body 7, and prevent air from escaping unintentionally during the administration process, i.e. when pressure is applied to the delivery container.

The flexible inner bladder 9 is securely attached to the delivery container 2 in such a manner that the inner cavity 8 defined by said bladder 9 can communicate with the air inlet, but that flow communication between the two cavities 6, 8 is effectively prevented. Thus the flexible inner bladder may be attached to a part of inner surface of the squeezable external body 7 by glue, a welding or a connector member, preferably only in the lower part of the delivery container.

Drawing air into the inner cavity 8 has the advantage that the size of the flexible bladder 9 increases, causing a change in the respective sizes of the cavities, i.e. when the size of the flexible bladder increases as air is drawn into said cavity, the size of the outer cavity 6 containing enema is reduced. In this way the enema device will always be perceived as "full of enema" by the user until the desired dosage or the entire enema content has been expelled from the device.

The closure member 4 is releasable attached to the delivery container 2 via an intermediate member 14, and by means of a first coupling unit 15. In the embodiment shown in the figures the coupling unit is in the form of a snap fit, comprising a first coupling part 16, placed on the closure member, and a second coupling part 17, placed on the intermediate member 14. A person skilled in the art will understand that the shown coupling unit 15 is one of many possibilities of removing and remounting the closure member 4, and that others, e.g. threaded coupling units and hinged lids with snap-fittings, also are contemplated within the scope of the present invention.

Said first and second coupling parts 16, 17 are arranged for engaging each other in order to lock the closure member 4 and the intermediate member 14 in a closed position, and for being released when e.g. a twisting action is applied on the outer surface 18 of the closure member 4 in relation to the delivery container 2. When such an action is provided, the first and second coupling parts 16, 17 will disengage each other, facilitating removal of the closing member 4 from the delivery container 2. The closing member 4 can then easily be remounted by simply clicking the closing member 4 back in placed, upon which the first and second coupling parts 16, 17 will engage and close the delivery container 2.

In order to prevent enema contained in the outer cavity 6 from escaping the cavity 6 unintentionally, it is preferred that a liquid tight seal between the first and second coupling parts 16, 17 is provided. Sealing rings (not shown) or the like, may be used, if necessary, in order to ensure that said seal is obtained.

The intermediate member is permanently and securely connected to the squeezable external body 7, e.g. using a glue, welding or similar means, thereby providing a reliable and durable construction, in which the closing member 4 in a simple manner can be removed from and remounted on the delivery container 2.

In the embodiment shown in the figures, the applicator nozzle 3 is removable connected to the delivery container 2 by means of a second coupling unit 19. This ensures that the applicator nozzle 3 can be removed after use and then be either cleaned, sterilised or simply discarded.

The second coupling unit 19 consist of a female coupling part 20 located in the closure member 4 and arranged for engaging a male coupling part 21 placed on the applicator nozzle 4. In the embodiment shown the male coupling part 21 is a short flexible tube 22, extending via an inner tube 23 in the applicator nozzle 4, to the exit opening 5. The female coupling part 20 is made of a rigid material, such that a liquid tight seal is provided between the two parts 20 and 21 when they are engaging. The male coupling part 21 has a tapered end for facilitating an simple engagement with the female part 20 when the male coupling part 21 is inserted into and retracted from the female coupling part 20.

The applicator nozzle further comprises an annular, substantially fructoconical extension 24, which not only provides a comfortable design for the user and a tight fit with the anal opening during the administration proceedings, but also a stop for limiting the extension of the male coupling part 21 into the female coupling part 20 when the two parts are connected. Thereby is an especially simple and inexpensive design of the enema device according to the invention obtained.

In order to provide a comfortable design without any sharp edges, the outer edge 25 of the fructoconical structure 24, flushes into the outer surface 18 of the closure member 4, which again flushes into the outer surface of the delivery container 2, as shown in the drawings.

FIG. 3 schematically illustrates the administration procedure using the first embodiment 1 of the enema device according to the invention.

In a first embodiment 1 according to the present invention the enema is placed in the outer cavity 6 which is communicating with the outlet 10, and air can be drawn into the inner cavity 8 though the air inlet 12.

In order to initiate the administration procedure, the applicator nozzle 3 is placed in the patients anal opening and it is ensured that the nozzle 3 provides a tight fit with the opening.

Compression force is then applied to the delivery container 2 by squeezing the hand holding the delivery container 2. The enema is allowed to flow through the outlet, into the tube 23 and out of the exit opening 5 in the applicator nozzle 3, resulting in the enema being injected into the rectum and colon.

When the user during the administration procedure releases the compression force on the squeezable external body 7, said body will resumes its original shape, and air will be drawn into the inner flexible bladder 9 via the air inlet 12. FIG. **3*a* shows the enema device 1 after a small amount of enema has been expelled and a corresponding amount of air has been introduced into the flexible inner bladder 9**.

Figures 3A, 3B, 3C, 3D:
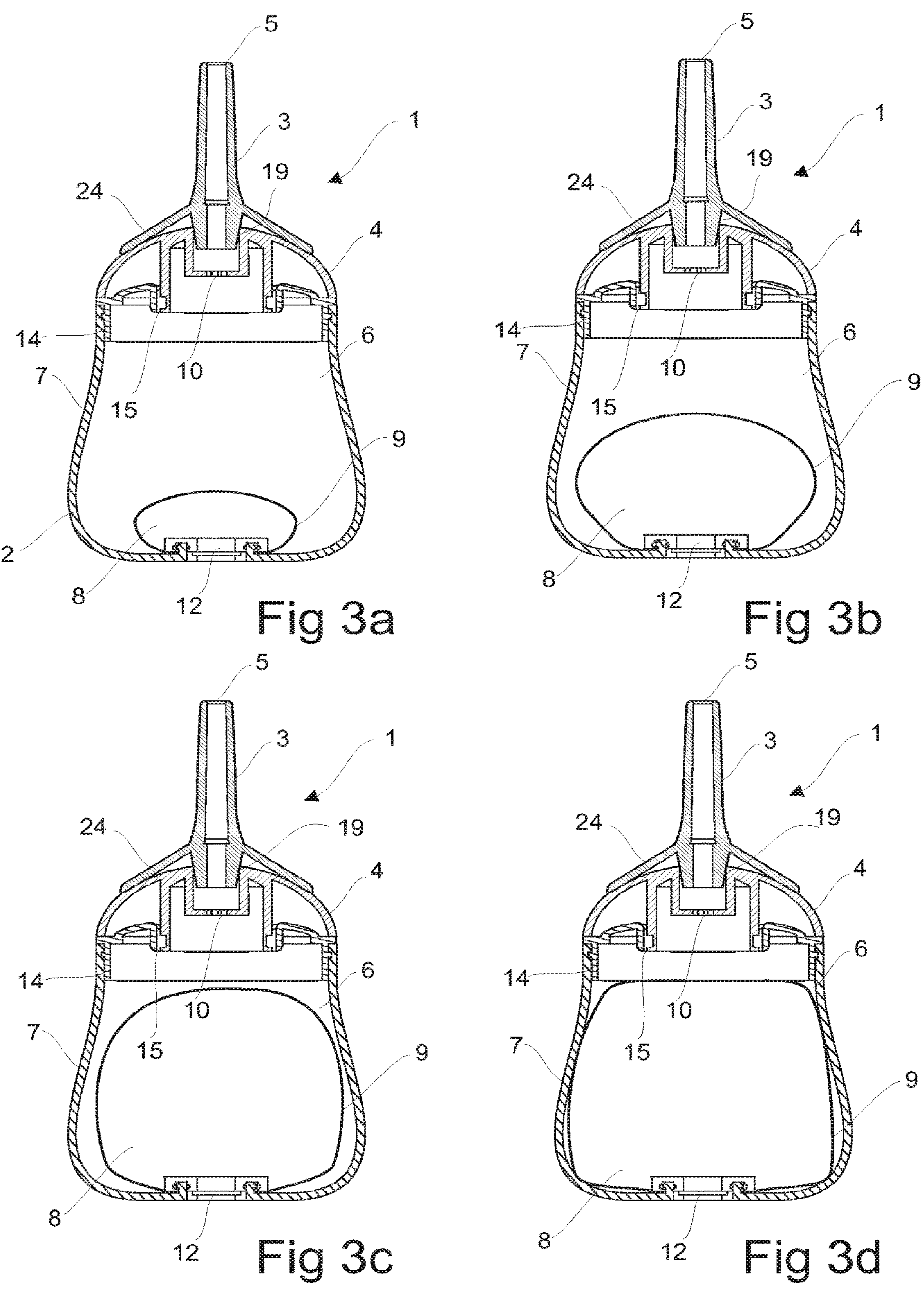

After each squeezing and subsequent release action more and more air will be drawn into the inner cavity 8, gradually increasing the size of the flexible bladder 9 and simultaneously reducing the size of the outer enema container cavity 6, as shown in FIGS. **3*a*, 3*b* and 3*c*. Thus, the air in the inner cavity 8 will function as a displacement fluid, forcing the enema in the outer cavity 6 towards the outlet 10, and the enema device 1 will always be perceived as "full" by the user, until the desired dosage of enema has been administered, or the entire enema content, as shown in FIG. 3*d* has been expelled from the device 1**.

As the outer cavity with the enema gradually is reduced, the user can easier expel the enema from the device according to the present invention, compared to the known enema devices.

Furthermore, since the inner 8 and outer cavity 6 cannot communicate with each other, air in the inner cavity 8 is effectively prevented from being mixed with the enema in the outer cavity 6. Accordingly, air cannot be administered into the patients colon and unnecessary discomfort caused by distending of the colon by air, is effectively prevented.

After the liquid is administrated into the rectum and/or colon the enema device 1 is removed from the anal opening, and the applicator nozzle 3 can be detached from the delivery container 2 and either be discarded or cleaned for later use.

Figure 4:
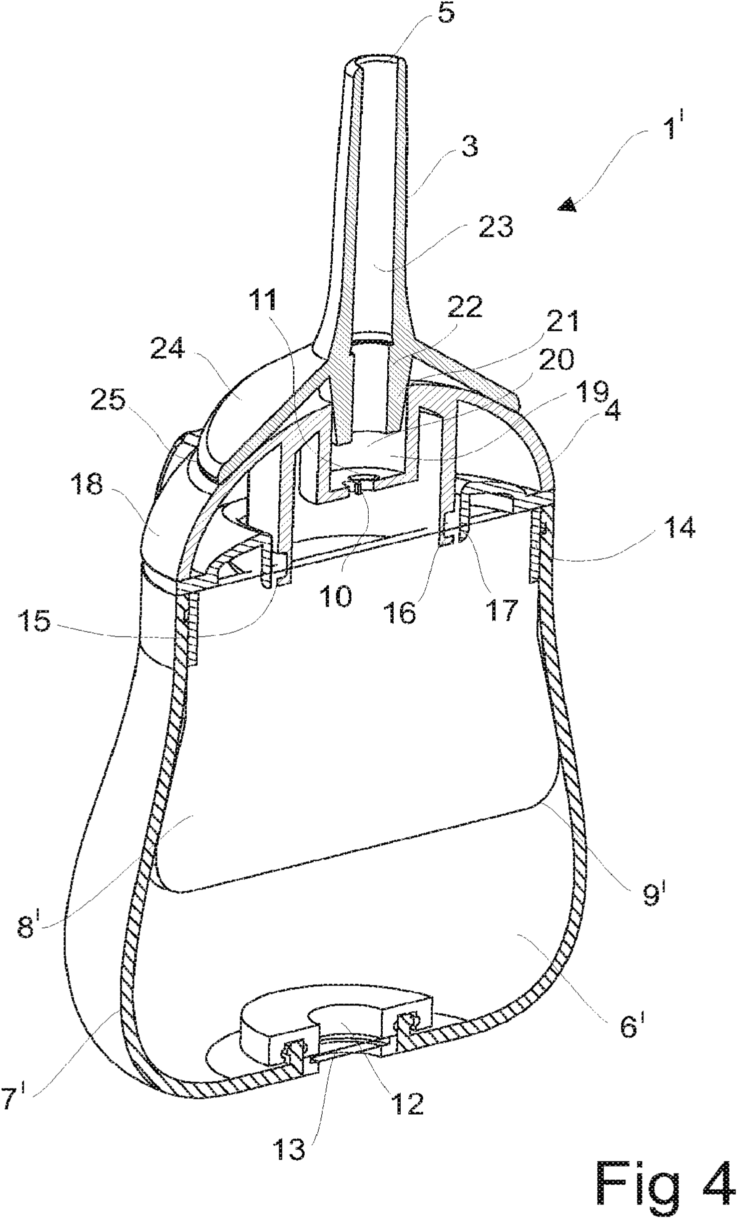

FIG. 4 shows a second embodiment 1' according to the present invention, this embodiment corresponds to the embodiments in FIG. 1-3, and for like parts the same reference numbers are used.

The second embodiment 1' differ from the first embodiment in that the cavities for accommodating the enema and air is reversed.

In the second embodiment the delivery container 2 also comprises two cavities, an outer cavity 6' and an inner cavity 8'. Said outer cavity 6' is being defined by an squeezable external body 7' arranged in communication with the air inlet, and said inner cavity 8' is defined by an inner flexible bladder 9' being in flow communicating with the exit opening 5 via an outlet 10.

Enema is accommodated in the inner flexible bladder 9' and will, when pressure/compression force is placed on the delivery container 2 via the squeezable external body 7' be expelled through the exit opening 5, in a manner similar to the first embodiment 1, as shown in FIG. 5*a*-5*d*.

Figures 5A, 5B, 5C, 5D:
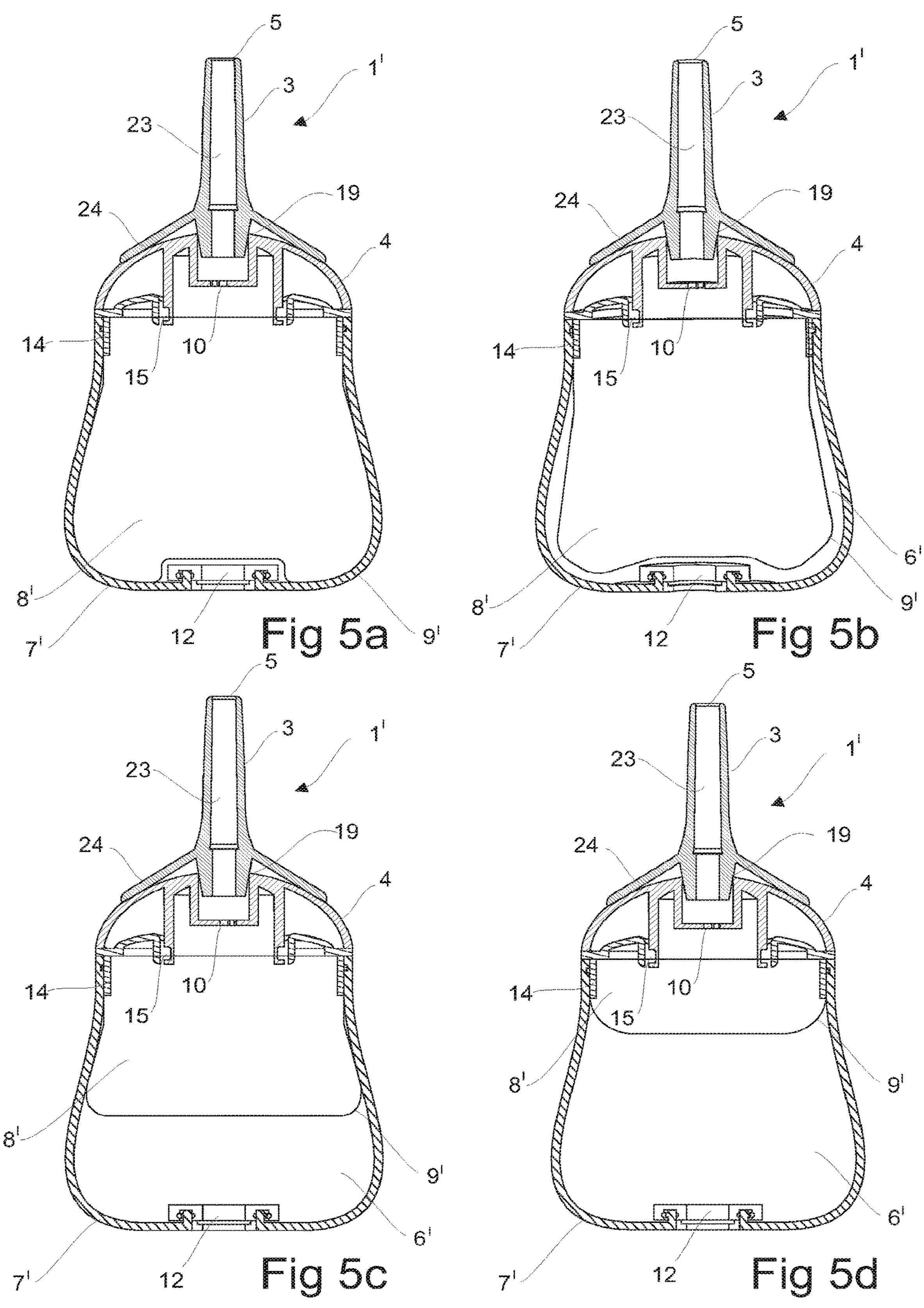

In short, FIG. 5*a* shows the second embodiment 1' of the enema device according to the invention in an initial position, i.e. where the device 1' is fully loaded with the enema and ready to be used. Compression force is then applied to the delivery container 2 whereby enema flows through the outlet 10, and out of the exit opening 5 in the applicator nozzle 3.

When the compression force on the squeezable external body 7' is released, said body will resumes its original shape, and air will be drawn into the outer cavity 6' via the air inlet 12.

FIG. 5*b* shows the enema device 1' after a small amount of enema has been expelled and a corresponding amount of air has been introduced into the outer cavity 6'. After each squeezing and subsequent release action more and more air will be drawn into the outer cavity 6', gradually reducing the size of the flexible bladder 9', as shown in FIG. 5*b*, 5*c*, 5*d*.

Thus, just as for the first embodiment 1, the air will function as a displacement fluid, forcing the enema in the flexible bladder 9' towards the outlet 10, thereby ensuring that the enema device 1' will be considered full whereby the user easily can expel the enema.

As for the first embodiment 1, the flexible inner bladder 9' of the second embodiment 1' is also securely attached to the delivery container 2 such that the inner cavity 8' communicate with the outlet 10, but that flow communication between the two cavities 6', 8' is effectively prevented, also when the closure member 4, is detached from the delivery container 2. As shown e.g. in FIG. 4, the flexible inner bladder 9' is securely attached to an upper part of the inner surface of the squeezable external body 7.

After use, the enema device can be restored to it's initial position by deflating the air cavity 8, 6' and refilling the enema cavity 6, 8' with enema.

This is obtained in the embodiments shown 1, and 1' by removing the closure member 4 providing an opening into the cavity in communication with the outlet i.e. the enema cavity whereby an easy manual refilling of enema into said cavity is possible. Simultaneously the pressure inside the enema cavity 6, 8' will drop whereby the combination valve 13 will release air from the air cavity 8, 6' deflating the air cavity.

After the air cavity 8, 6' has been emptied, the user can easily refill the enema cavity 6, 8' with enema, and remount the closure member on the delivery container, whereby the enema device according to the invention is ready for the next enema administration.

In the embodiments shown 1, 1', the closure member 4 is removed by applying a twisting action on the outer surface 18 of the closure member 4 whereby the first and second coupling parts 16, 17 are disengaged and the closure member 4 can be removed. The closing member 4 can then easily be remounted by simply clicking the closing member 4 back in placed, upon which the first and second coupling parts 16, 17 will engage and close the delivery container 2.

It should be noted that the closure member may be releasable attached to the delivery container by other suitable means, and said opening/removal and remounting procedure may be adjusted accordingly.

Since the device according to the invention are relatively small and intended for use with a single hand, it can used equally well for both home-administrations of enema or for the use in medical or hospital facilities where larger irrigations/enema devices are too troublesome and complicated to use.

A person skilled in the art will understand that the enema device accordingly to the invention can be combined with electronical means arranged to automatically expel the enema from said device, e.g. electronic pumping means.

Modifications and combinations of the above principles and designs are foreseen within the scope of the present invention.

The invention claimed is:

1. An enema device comprising a delivery container and an applicator nozzle, wherein said delivery container comprises two distinct cavities, an outer cavity defined by a squeezable external body, and an inner cavity defined by an inner flexible bladder, and wherein one of said two cavities is communicating with an outlet for dispersing an enema though the applicator nozzle and another one of said two cavities is communicating with surroundings via an air inlet, wherein the cavity communicating with the air inlet is arranged for becoming larger during intake of air, and the cavity communicating with the outlet is arranged for becoming smaller during intake of air, whereby an enema contained in the cavity communicating with the outlet is displaced towards said outlet, and wherein an increase in volume of the cavity communicating with the air inlet causes a corresponding reduction in volume of the cavity communicating with the outlet, such that expansion of the cavity communicating with the air inlet compresses the cavity containing the enema to displace the enema toward the out let, and wherein a first nonreturn valve is placed in communication with the outlet, and/or a second nonreturn valve is placed in communication with the air inlet.

2. The enema device according to claim 1, wherein the enema device is arranged such that when an entire content of enema has been expelled from the delivery container, the cavity communicating with the air inlet fills out an entire inner volume of the squeezable external body.

3. The enema device according to claim 1, wherein the enema is accommodated in the outer cavity, said outer cavity is communicating with the outlet, and the inner cavity is communicating with the surroundings via the air inlet.

4. The enema device according to claim 1, wherein enema is accommodated in the inner cavity, said inner cavity is communicating with the outlet, the outer cavity is communicating with the surroundings via the air inlet.

5. The enema device according to claim 1, wherein the inner and outer cavity are not in flow communication.

6. The enema device according to claim 1, wherein the air inlet is placed in the enema device at a position separate from the applicator nozzle.

7. The enema device according to claim 6, wherein the air inlet is placed opposite the applicator nozzle.

8. The enema device according to claim 7, wherein air in the cavity communicating with the air inlet is released through a release valve, and wherein there is a physically connection between the release valve and the closure member such that when the closure member is removed/opened, said physically connection activates the release valve.

9. The enema device according to claim 8, wherein said release valve is placed near the second non-return valve.

10. The enema device according to claim 1, wherein the enema device is arranged for deflating the cavity communicating with the air inlet.

11. The enema device according to claim 1, wherein the enema device is arranged for being opened and closed.

12. The enema device according to claim 1, wherein the enema device comprises a closure member arranged for being releasably attached to the delivery container.

13. The enema device according to claim 12, wherein the closure member is arranged for being releasably attached to the delivery container by means of a first coupling unit.

14. The enema device according to claim 12, wherein the outlet is placed in the closure member, and wherein the enema device is arranged such that when the closure member is opened/removed there is only access to the cavity communicating with the outlet.

15. The enema device according to claim 12, wherein the enema device is arranged for releasing the air in the cavity communicating with the air inlet, to the surroundings when the closure member is opened/removed from the delivery container.

16. The enema device according to claim 12, wherein the closure member is made of a rigid material, and releasably attached to the delivery container via an intermediate member.

17. The enema device according to claim 12, wherein the enema device is arranged for providing a fluid tight seal between the closure member and the deliver container.

18. A method of refilling the enema device according to claim 12, said method comprises the following consecutive steps:

opening the delivery container,
deflating the cavity communicating with the air inlet,
refilling the cavity communicating with the outlet, and
closing the delivery container;

wherein air in the cavity communicating with the air inlet automatically is expelled to the surroundings when the closure member is opened/removed from the delivery container.

19. The enema device according to claim 1, wherein air in the cavity communicating with the air inlet is released through a release valve, which is activated when the pressure drops in the cavity communicating with the outlet, or when the pressure in the cavity communicating with the air inlet exceeds a predetermined limit.

20. The enema device according to claim 19, wherein the air inlet and the release valve are combined in a dual function valve, a lip valve, a duck bill valve, an umbrella valve, a dome valve, and/or a combination valve.

21. The enema device according to claim 20, wherein the dual function valve is a diaphragm valve.

22. The enema device according to claim 20, wherein the combination valve is an umbrella/duckbill combination valve.

23. The enema device according to claim 1, wherein the delivery container has a shape arranged to fit into a user's hand.

24. The enema device according to claim 23, wherein the shape of the delivery container is one of an elongated spherical shape, an oval shape and a bulb shape.

25. The enema device according to claim 23, wherein the outer cavity is arranged as a handheld pump made of a resilient deformable material with a memory.

26. The enema device according to claim 25, wherein the resilient deformable material includes silicone.

27. The enema device according to claim 1, wherein the inner flexible bladder defining the inner cavity is made of a material arranged for expanding/unfolding and collapsing in response to an amount of fluid (air or enema) placed in said cavity, for preventing any exchange of fluid between the inner and outer cavity, and for not reacting with the enema and air.

28. The enema device according to claim 1, wherein the applicator nozzle has a mainly frustoconical shape whose outside diameter progressively decreases from its proximal end to its distal end.

29. The enema device according to claim 1, wherein the applicator nozzle is arranged as a plug forming a sealing fit with the anal opening.

30. The enema device according to claim 1, wherein the applicator nozzle is provided with a lubricant or an activated hydrophilic coating.

31. A method of refilling the enema device according to claim 1, said method comprises the following consecutive steps:

opening the delivery container,
deflating the cavity communicating with the air inlet,
refilling the cavity communicating with the outlet, and
closing the delivery container.

* * * * *